(12) United States Patent
Belshaw et al.

(10) Patent No.: US 7,820,412 B2
(45) Date of Patent: Oct. 26, 2010

(54) METHOD OF ERROR REDUCTION IN NUCLEIC ACID POPULATIONS

(75) Inventors: Peter Jeremy Belshaw, Madison, WI (US); Michael R. Sussman, Madison, WI (US); Franco Cerrina, Madison, WI (US); James Howard Kaysen, Madison, WI (US); Brock F. Binkowski, Sauk City, WI (US); Kathryn E. Richmond, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/214,201

(22) Filed: Aug. 29, 2005

(65) Prior Publication Data

US 2006/0127926 A1 Jun. 15, 2006

Related U.S. Application Data

(60) Provisional application No. 60/604,867, filed on Aug. 27, 2004.

(51) Int. Cl.
*C12P 19/34* (2006.01)
(52) U.S. Cl. .................................... 435/91.2
(58) Field of Classification Search .............. 435/6
See application file for complete search history.

(56) References Cited

U.S. PATENT DOCUMENTS

| 6,114,115 | A | 9/2000 | Wagner, Jr. |
| 6,375,903 | B1 | 4/2002 | Cerrina et al. |
| 6,991,922 | B2 * | 1/2006 | Dupret et al. ............ 435/91.1 |
| 2005/0227235 | A1 | 10/2005 | Carr et al. |
| 2005/0255477 | A1 | 11/2005 | Carr et al. |

FOREIGN PATENT DOCUMENTS

| WO | WO99/42813 | | 8/1999 |
| WO | WO 99/54498 | * | 10/1999 |
| WO | WO02/095073 | | 11/2002 |
| WO | WO 03/054232 | * | 7/2003 |
| WO | WO 03/072832 | | 9/2003 |
| WO | WO 2004/090170 | | 10/2004 |

OTHER PUBLICATIONS

Singh-Gasson et al. Nature Biotechnology, vol. 17, pp. 974-978, 1999.*
Kikuchi et al. Gene, vol. 236, pp. 159-167, 1999.*
Biswas, I., et al., "Identification and Characterization of Thermostable MutS Homolog from *Thermus aquaticus*," J. of Biological Chemistry 271:5040-5048 (1996).
Golz, S., et al., "Enzymatic mutation detection: enrichment of heteroduplexes from hybrid DNA mixtures by cleavage-deficient GST-tagged endonuclease VII," Nucleic Acids Research 27:i-iv (1999).
Stemmer, W.P.C., "Rapid evolution of a protein in vitro by DNA shuffling," Letters to Nature 370:389-391 (1994).
Nelson, S.F., "Genomic mismatch scanning: Current progress and potential applications," Electrophoresis, vol. 16, No. 2, pp. 279-285 (1995).
Binkowski, Brock F., et al., "Correcting errors in synthetic DNA through consensus shuffling," Nucleic Acids Research, vol. 33, No. 6, ISSN: 0305-1048 (2004).
Carr, Peter A., et al.,"Protein-mediated error correction for de novo DNA synthesis," Nucleic Acids Research, vol. 32, No. 20, ISSN: 0305-1048 (2004).

* cited by examiner

*Primary Examiner*—Gary Benzion
*Assistant Examiner*—Cynthia B Wilder
(74) *Attorney, Agent, or Firm*—Sara D. Vinarov; Quarles & Brady LLP

(57) ABSTRACT

A method is disclosed for the direct synthesis of double stranded DNA molecules of a variety of sizes and with any desired sequence. The DNA molecule to be synthesis is logically broken up into smaller overlapping DNA segments. A maskless microarray synthesizer is used to make a DNA microarray on a substrate in which each element or feature of the array is populated by DNA of a one of the overlapping DNA segments. The complement of each segment is also made in the microarray. The DNA segments are released from the substrate and held under conditions favoring hybridization of DNA, under which conditions the segments will hybridize to form duplexes. The duplexes are then separated using a DNA binding agent which binds to improperly formed DNA helixes to remove errors from the set of DNA molecules. The segments can then be hybridized to each other to assemble the larger target DNA sequence.

15 Claims, 3 Drawing Sheets

METHOD OF ERROR REDUCTION IN NUCLEIC ACID POPULATIONS

CROSS REFERENCE TO RELATED APPLICATION

This application claims the benefit of U.S. Provisional Application No. 60/604,867 filed Aug. 27, 2004.

STATEMENT REGARDING FEDERALLY SPONSORED RESEARCH OR DEVELOPMENT

This invention was made with United States government support awarded by the following agencies: DOD ARPA DAAD19-02-2-0026. The United States has certain rights in this invention.

BACKGROUND OF THE INVENTION

This invention pertains generally to the field of biology and particularly to techniques and apparatus for the manufacture of DNA molecules of defined or desired sequences. The manufacture of DNA molecules also makes possible the synthesis of any desired peptides, proteins or assemblies of proteins and nucleic acids as may be desired.

Using the techniques of recombinant DNA chemistry, it is now common for DNA sequences to be replicated and amplified from nature and for those sequences to then be disassembled into component parts which are then recombined or reassembled into new DNA sequences. While it is now both possible and common for short DNA sequences, referred to a oligonucleotides, to be directly synthesized from individual nucleosides, it has been thought to be generally impractical to directly construct large segments or assemblies of DNA sequences larger than about 400 base pairs. As a consequence, larger segments of DNA are generally constructed from component parts and segments which can be purchased, cloned or synthesized individually and then assembled into the DNA molecule desired.

For example, if an expression vector is desired to express a new protein in a selected host, the scientist can often purchase a generic expression vector from a molecular biology supply company and then clone or synthesize the protein coding region for the gene sought to be expressed. The coding region must be ligated into the vector in such a manner and in the correct location and orientation such that the vector will be effective to express the desired protein in the host. The purchaser of the vector must also examine the sequence of the vector to make sure no other DNA component of the vector has other properties that might be detrimental to the experiment the purchaser wishes to run. Thus, the difficulty in constructing any new desired larger DNA construct is dependent on what similar constructs, or what components of the construct, can be purchased or obtained from public sources, and how much information is available about the sequences of those components.

A novel methodology to construct and assemble newly designed DNA sequences of indefinite length has been developed based on the use of DNA constructed in DNA microarrays. A DNA microarray is made up of a plurality of sets of single stranded DNA probes arranged on a substrate. The sets of probes are identical in nucleotide sequence but different in sequence from other sets of probes. A technique has been described for the in situ synthesis of DNA microarrays that is adapted for the manufacturing of customized arrays. Published PCT patent application WO99/42813 and U.S. Pat. No. 6,375,903 describe a method for making such arrays in which the light is selectively directed to the array being synthesized by a high density micromirror array under software control from a computer. Since the micromirror array is operated totally under software control, the making of complex and expensive photolithographic masks is avoided in its entirety. It has been previously proposed that such custom microarrays can be used to provide the single stranded DNA segments necessary and sufficient to assemble double stranded DNA molecules of indeterminate length. In PCT published patent application WO 02/095073, the disclosure of which is hereby incorporated by reference, this process is set forth. In short, using that approach, short segments of single stranded DNA are made on the microarray and designed such that a portion of each probe is complementary to two other oligonucleotides in another set on the array. In theory then, when the oligonucleotides are released from the substrate of the array, the DNA segments will self-assemble into the complete desired DNA molecule as each complementary segment hybridizes to its complement.

A complexity arises from this general approach to DNA synthesis that no synthetic or biochemical processes are ever completely efficient and accurate. Thus it is inevitable that there will be occasional deletion and substitution errors in the DNA segments made by this process. To facilitate the practical synthesis of longer DNA molecules on interest and of good quality, methods must be developed to purify the DNA sequences of interest from those artifacts that arise through various sorts of errors and inefficiencies in the probe synthesis and assembly process.

One process for error correction has previously been proposed, a process referred to as coincidence filtering. That process is optimized for the detection and removal of rare single base pair errors in long DNA sequences.

BRIEF SUMMARY OF THE INVENTION

The present invention is summarized in a method for separation of DNA molecules of correct sequence away from DNA molecule of incorrect sequence, the method including the steps of exposing a solution of small fragments of double stranded DNA molecules to a DNA binding agent which will binds selectively to duplex DNA molecules having a topographical irregularity; and separating the DNA molecules to which the DNA binding agent bound from those DNA molecules to which the DNA binding agent did not bind.

This invention makes practical the construction to order of DNA constructs of virtually any size with minimal error. This frees the experimenter who wishes to perform experiments on DNA or on gene expression from the constraints of working with commercially available vectors or genetic elements. Instead, DNA sequences can be invented on a computer and fabricated for the first time and in a short time period using this microarray based technique.

The present invention is also directed to a method for separating out DNA duplexes carrying a minority sequence from a pool of such sequences carrying a majority sequence. This method includes the steps of denaturing the duplex DNA molecules; permitting the DNA molecules to hybridize to form new DNA duplex molecules; exposing the duplex DNA molecules to a DNA binding agent that binds selectively to DNA molecules having an irregularity in the topology of the DNA duplex; and separating the DNA molecules by separation out of those DNA molecules to which the DNA binding agent bound.

Further objects, features and advantages of the invention will be apparent from the following detailed description when taken in conjunction with the accompanying drawings.

DETAILED DESCRIPTION OF THE INVENTION

In one embodiment, the present invention originated as a method for reducing the amount of error produced during the synthesis of double stranded oligonucleotides. We refer to the method described here as "consensus shuffling". The method has this name since it is designed to identify and isolate the DNA duplexes which represent the consensus sequences in a population of duplexes with some error sequences. This method differs from an earlier error correction method known as "coincidence filtering." Both processed are intended to remove from the nucleic acid populations those nucleic acids that have mismatches or deletions internally within them. The overall process also includes a method to selectively filter out any double stranded DNA molecules which have a correct, matched sequence but have a sequence that is different from the sequence of the majority of DNA sequences in the population of DNA molecules made. The two processes differ in the detail of their methodology. In consensus shuffling, DNA sequences under assembly are either assembled into shorter fragment or are digested into shorter fragments, and then permitted to hybridize. The double stranded shorted fragments are then exposed to a selective DNA filtering agent, such as MutS, which removes mismatched sequences from the population of sequences. Then the surviving fragments are used as templates for PCR amplification and assembly into larger sequences.

The coincidence filter methodology works well for larger DNA sequences with single errors in them. As this technology has been put into practice, however, the fact that most DNA synthesis processes have low, but inevitable, error rates becomes more significant. Long DNA sequence synthesized artificially turn out to result in populations of DNA strands where virtually all members of the population have multiple errors in them. Consensus shuffling works to remove errors by, as the name implies, re-shuffling the sequences toward the consensus sequence in a population, thus eliminating errors that are the result of random erroneous nucleotide addition. This method is based on the theory that the consensus sequence will be the correct one.

Figure 1:
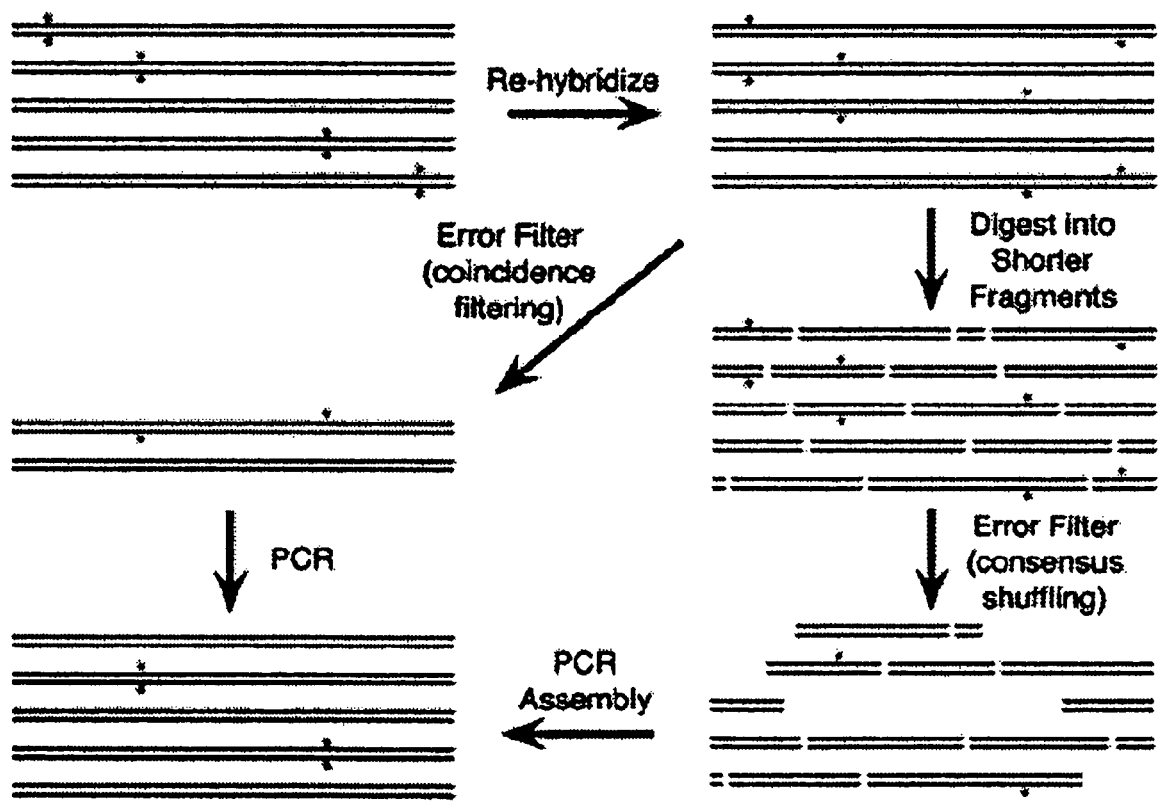
FIG. 1 is a simplified drawing showing the overall process of the present invention.

Error correction by consensus shuffling is outlined in FIG. 1. The population of double stranded DNA molecules resulting from DNA synthesis will contain random errors. The population of DNA molecules is first re-hybridized to create now double stranded molecules, which will inevitably contain mismatches. Then the duplex molecules are cleaved enzymatically into small overlapping fragments. The fragments which contain mismatches are then selectively removed through absorption to MutS, or other binding molecule which will selectively bind to DNA with topological abnormalities. The remaining fragments in the population are thus enriched in the correct sequence. Those fragments then serve as templates for assembly PCR to produce full-length products. This process can be iterated as many times as needed until the consensus sequence becomes the dominant species in the population, as will inevitable occur. This approach shares some aspects with DNA shuffling (Stemmer, *Nature*, 370, 389-391 (1994)), but with additional mismatch exposure and removal steps. FIG. 1 also outlines the application of the MutS filter on full-length gene assembly products, a process we term coincidence filtering. In coincidence filtering, error-containing heteroduplexes are directly removed from gene assembly products. However, if random errors exist in virtually all members of a DNA population, coincidence filtering will be ineffective and consensus shuffling will be required for effective error removal. As such, the two processes can effectively work together, by performing consensus shuffling until a consensus sequence is reached and then using coincidence filtering to remove any remaining errors from the population.

The method of the present invention arose out of efforts to make a general purpose DNA synthesis process using the massively parallel DNA fabrication capabilities of the maskless DNA synthesis instrument, of the type described in U.S. Pat. No. 6,375,903, the disclosure of which is also incorporated herein by reference. The maskless array synthesizer permits many single stranded DNA probes to be fabricated in parallel in a short time, under computer control. This technology permits the manufacture in a few hours of a custom DNA microarray in which the single stranded DNA probes in the array can be of any arbitrary DNA sequence. The microarray is arranged in features where all the probes in a given feature are of the same DNA sequence, which can differ from the sequence of the probes in any other feature. This technology permits the synthesis of tens to hundreds of thousands of different features in a single microarray, each feature composed of DNA probes of 20 to 150 nucleotides in length, in a matter of hours. Here, the microarray synthesis instrument is used as a massively parallel generator of single stranded DNA segments, and the process described here is concerned with assembling those segments into a long piece of DNA while eliminating errors in the synthesis process.

The technology described in the previously mentioned PCT published application WO 02/095073 already envisions the use of the massively parallel DNA synthesis capability of the maskless array synthesizer to be used to make very long DNA sequences of interest. The present invention is directed toward processes for solving, among other things, the following problem. Consider that every step in the addition of nucleotides to the DNA probes in the microarray is 99% efficient and accurate. That level of efficiency would mean that for every 100 nucleotides added, one nucleotide is either not added at all or is added in the wrong place. This rate of error would mean that if the DNA segments are all 25-mers, or composed of oligonucleotides 25 nucleotides in length, one out of every four probes, on average, would have an error in it. While the actual efficiency can, in reality, be made higher than 99%, the error rate cannot even be zero. Some number of the probes will have an error. The error can be any of the following: a failure to add a nucleotide, i.e. a deletion; an addition of a nucleotide in an incorrect location, i.e. an addition; a complete misplacement of one nucleotide for another, i.e. a substitution; or a chemical modification of a nucleotide. The purification process should therefore be arranged so as to remove from the population sequences made during the hybridization process as many as possible of the probes that contain an error, regardless of the type of error. The method described here will do that. It should be understood that while this process in designed and intended to solve this specific problem of DNA purification and separation in the context of using the microarray technique for DNA synthesis, this same process will be useful in any other DNA synthesis procedures in which it is desired to ultimately obtain copies of a single DNA molecule of interest.

The main requirements for the DNA binding agent for use in this process is that it binds preferentially to double stranded DNA having a sequence mismatch between its two strands. The preferred agent is MutS, a bacterial protein. MutS from *Thermus aquaticus* can be purchase commercially from the Epicenter Corporation, Madison, Wis., Catalog No. SP72100 and SP72250. The gene sequence for the protein is also known and published in Biswas and Hsieh, *Jour. Biol. Chem.* 271:5040-5048 (1996) and is available in GenBank, accession number U33117. It is therefore readily possible for those of skill in the art to use conventional gene expression vectors transformed into bacteria in culture to produce this protein as well. Another molecule which might be used as the DNA binding agent in this process is CEL1 endonuclease from celery which has a high specificity for insertions, deletions and base substitution mismatches and can detect two polymorphisms which are five nucleotides apart form each other. It is also possible to design and synthesize small organic molecules which will bind to specific nucleotide mismatches, such as dimeric napthyridine 1, a synthetic ligand that binds to a G-G mismatch. A cocktail of such ligands which, in combination, recognize all possible mismatches could replace MutS. Other protein agents that can differentiate between matched and unmatched duplexes could also be used. For example, the T7 endonuclease I will specifically cleave a DNA strand at a mismatch, and it would be possible to use this enzyme as a catalytic destroyer of mismatched sequences or to inactivate the cleavage function of this enzyme for use in this process as a mismatch binding agent. T4 endonuclease VII will specifically bind and cleave DNA at duplex mismatches and a mutant version of this enzyme has already been engineered that lacks the nuclease activity but retains the ability to bind mutant duplex DNA molecules. Golz and Kemper, *Nucleic Acids Research*, 27:e7 (1999). SP nuclease is a highly active nuclease from spinach that incises all mismatches except those containing a guanine residue, and this enzyme could also be engineered to remove the cleavage activity or used directly. Two or more of these binding agents could be combined to either provide further stringency to the filtration or to cover all types of sequence errors if one agent does not bind to all possible mismatches.

It is understood that the invention is not confined to the particular embodiments set forth herein as illustrative, but embraces all such modified forms thereof as come within the scope of the following claims.

EXAMPLES

To create an error filter, we constructed a fusion protein between Maltose Binding Protein (MBP) and the mismatch binding protein from *Thermus aquaticus* (MutS) with a C-terminal His6 tag (MBP-MutS-H6). MBP-MutS-H6 was overexpressed and purified from *E. coli* to greater than 95% purity. MBP-MutS-H6 immobilized on amylose resin was shown to selectively retain a 40-mer heteroduplex containing a deletion mutation over wt homoduplex.

Figure 2:
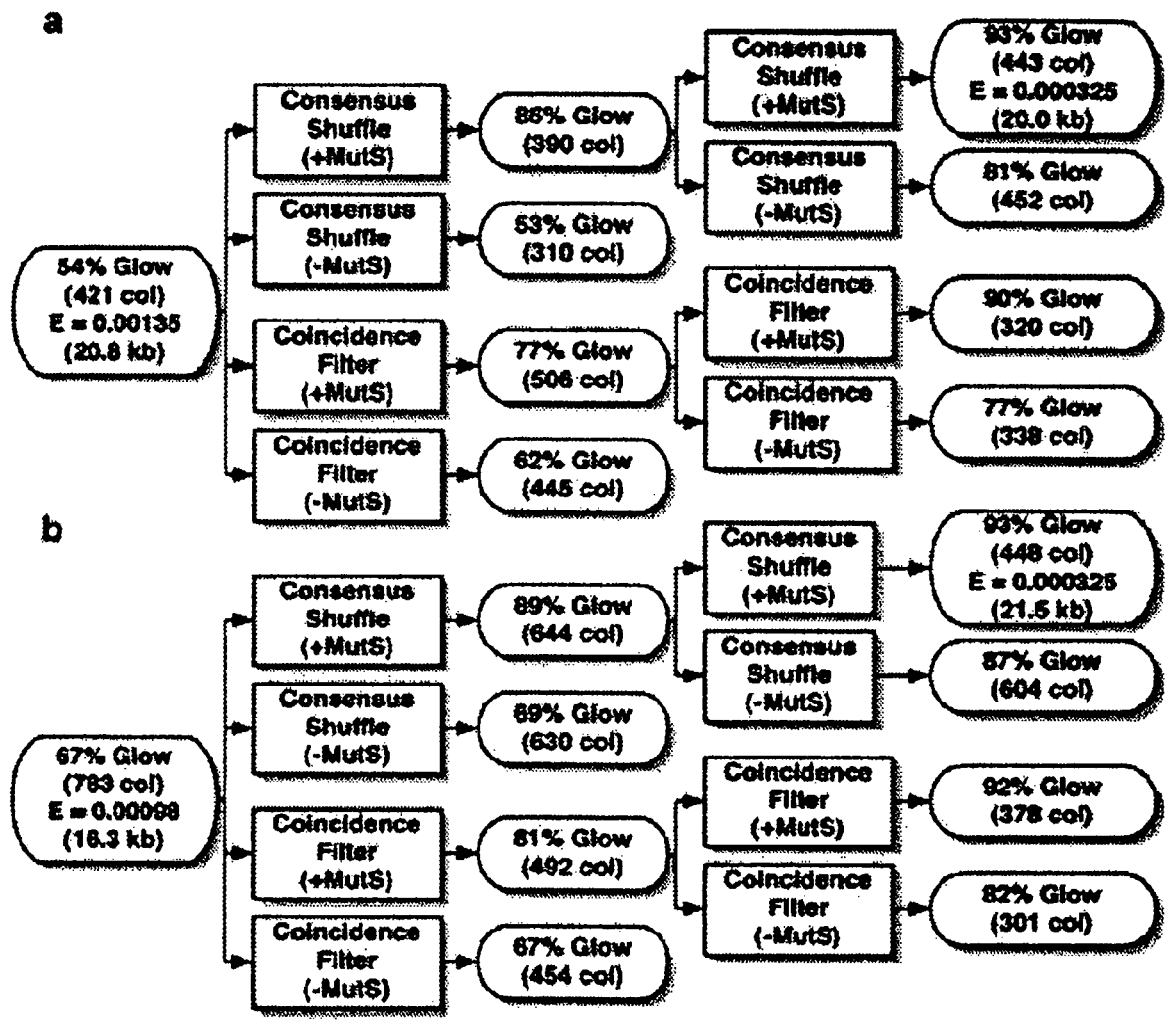
FIG. 2 illustrates the reduction in error rates achieved by the present invention as applied to the example described below.

To demonstrate error correction, unpurified 40-mer oligonucleotides were assembled by PCR to produce a 760 bp gene encoding green fluorescent protein (GFPuv). Two independent preparations of GFPuv containing typical gene synthesis errors (Table 1) were re-hybridized and subjected to two iterations of coincidence filtering or consensus shuffling. For consensus shuffling, each population was split into three pools and cleaved with distinct restriction endonucleases, producing fragments with an average size of 150 bp and a size range of 4-396 bp. Fragments were pooled and subjected to error filtering with or without added MBP-MutS-H6. The unbound fragments were reassembled into full-length products and PCR amplified. For coincidence filtering, unbound GFPuv was PCR amplified following treatment with the error filter. After cloning in *E. coli*, error rates were estimated by scoring colonies for fluorescence under a handheld UV lamp. Actual error rates of the input and consensus shuffled populations were determined by sequencing plasmid DNA from randomly selected colonies (FIG. 2). The results show that two rounds of consensus shuffling increased the percentage of fluorescent colonies from ~60% to >90% and reduced the error rate of the populations 3-4 fold from ~1.17 to ~0.31 errors/kb. MutS was required to increase the fraction of fluorescent colonies in each round of error filtering. The consensus shuffled population showed significant reductions in deletions and G-A mutations, consistent with the previously reported selectivity of *T. aq.* MutS (Table 1).

TABLE 1

Sequence errors in input and consensus shuffled DNA

| Mismatch | deletion | insertion | AG | AC | AA | TC | TG | TT | CC | GG |
|---|---|---|---|---|---|---|---|---|---|---|
| Input DNA | 18 | 1 | 2 | 10 | 0 | 3 | 6 | 0 | 2 | 1 |
| Consensus Shuffling | 3 | 0 | 3 | 0 | 0 | 2 | 2 | 0 | 2 | 0 |

A simple mathematical model (equations 1-6) was constructed to estimate some parameters of consensus shuffling. An input population of dsDNA molecules of length N, containing E errors/base is re-hybridized, fragmented into shorter dsDNA fragments of average length S, error filtered and reassembled. P(F) is the probability a fragment of length S will have a correct sequence. We determine the probability that re-hybridized duplexes will have zero (C), one (H) or both (I) strands with errors. Equation 5 estimates the probability that a fragment will be correct after a cycle of MutS filtering, P(F'), by applying a MutS selectivity factor (M) to adjust the relative amounts of mismatch containing duplexes (I,H) while accounting for the total fraction of correct strands in the re-hybridized duplexes. The probability of obtaining an error free assembly product, P(A), is then given by equation 6.

$$P(F) = (1 - E)^S \tag{1}$$

$$C = P(F)^2 \tag{2}$$

$$I = (1 - P(F))^2 \tag{3}$$

$$H = 1 - I - C \tag{4}$$

$$P(F') = \frac{2C + H/M}{2C + 2H/M + 2I/M} \tag{5}$$

$$P(A) = P(F')^{N/S} \tag{6}$$

Figure 3:
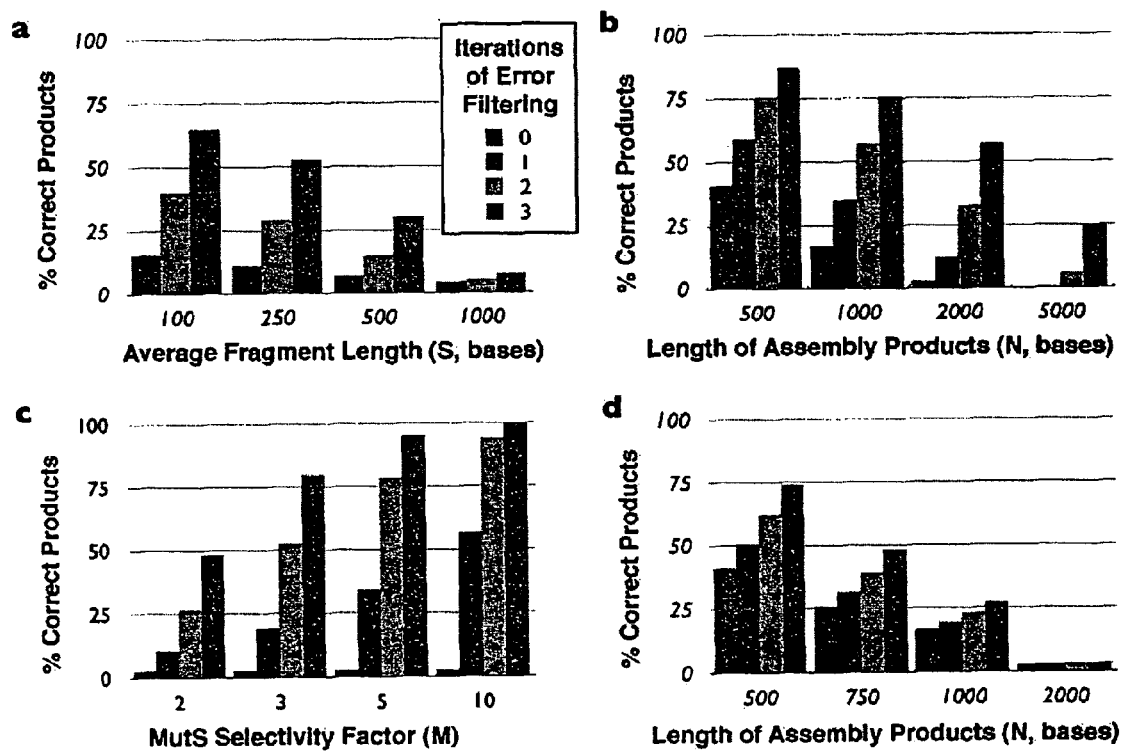
FIG. 3 presents graphical data from the examples below.

From the consensus shuffling error rate data, we estimate the MutS selectivity factor M to be ~2.2. FIG. 3 shows some predictions that emerge from this model assuming typical length (2 kb), fragment sizes (200 bp) and error rates (1.8/kb). Consensus shuffling is predicted to be most effective with smaller fragment sizes (FIG. 3a) and multiple iterations of MutS filtering can have dramatic results on populations with few correct sequence (FIG. 3b). The model also predicts that even modest improvements in the MutS selectivity factor through optimizing the binding conditions and/or using a more selective MutS homolog could dramatically improve consensus shuffling (FIG. 3c). Coincidence filtering (N=S) is predicted to be effective for populations with low errors/clone (FIG. 3d) but becomes ineffective when the majority of re-hybridized duplexes containing mismatches.

Although DNA shuffling has traditionally been used to create diverse populations through combinatorial shuffling of mutations in the population, the creation of diversity from a small population of mutants also demands an equivalent reduction in diversity among the shuffled products. Indeed, with consensus shuffling it should be possible to start with a population of DNA molecules wherein every individual in the population contains errors, and create a new population where the dominant sequence is the consensus sequence. To demonstrate this, ten non-fluorescent GFPuv clones with 1-2 distributed mutations each were pooled and subjected to either DNA shuffling alone or two iterations of consensus shuffling and cloned in E. coli. DNA shuffling alone (no MBP-MutS-H6) increased the percent fluorescent colonies to 30% (387 colonies total), similar to a previous report. Two rounds of consensus shuffling gave a new population that was 82% fluorescent (551 colonies total) indicating that the dominant species was now the consensus sequence of the input population.

We have demonstrated consensus shuffling and coincidence filtering as experimental methods to significantly reduce errors in synthetic gene populations. Coincidence filtering is a simple and effective procedure to reduce errors in DNA populations with low error rates/clone while consensus shuffling should be generally applicable for error correction in synthetic DNA populations of typical lengths and error rates. The consensus shuffling method is rapid (~6 hours/iteration) greatly reducing the time required to manually correct errors. These method should significantly increase the speed and accuracy with which we can "write" long DNA sequences.

Methods

Gene Assembly

Sequence 261-1020 of pGFPuv (Genbank Acc # U62636 with T357C, T811A, and C812G base substitutions) was assembled using unpurified 40 mer and 20 mer oligonucleotides (Qiagen) with 20 bp overlap. Assembly reactions contained the following components: 64 nM each oligonucleotide, 200 µM dNTPs, 1 mM MgSO$_4$, 1× buffer, and 0.02 units/µL KOD Hot Start DNA Polymerase (Novagen). Assembly was carried out using 25 cycles of 94° C. for 30 seconds, 52° C. for 30 seconds, and 72° C. for 2 minutes. PCR amplification of assembly products contained the following components: 10-fold dilution of assembly reaction, 25 µM of 20 bp outside primers, 200 µM dNTPs, 1 mM MgSO$_4$, 1× buffer, and 0.02 units/µL KOD Hot Start DNA Polymerase. PCR was carried out using 35 cycles of 94° C. for 30 seconds, 55° C. for 30 seconds, and 72° C. for 1 minute followed by a final extension at 72° C. for 10 minutes. PCR products were purified using the Quiagen quiaquick PCR purification kit with elution of dH$_2$O and concentrated.

Heteroduplex Generation

Assembled GFPuv was diluted to 250 ng/µL in 10 mM Tris-HClpH=7.8, 50 mM NaCl and heated to 95° C. for 5 minutes followed by cooling 0.1° C./second to 25° C.

Gene Fragmentation

Heteroduplex for consensus filtering was split into 3× pools and digested to completion with Nla III, (NEB) Taq 1(NEB), or NcoI plus XhoI (Promega) for 2 hrs following manufacturer's protocols. Digests were purified using the Qiagen qiaquick (PCR purification kit with elution in dH2O. Samples were pooled and the concentration was determined by measuring $A_{260}$.

MutS Binding

MutS binding reactions contained ~11.5 ng/µL DNA and ~950 nM MBP-MutS-H6 dimers in 1× binding buffer (20 mM Tris-HC1 pH=7.8, 10 mM NaCl, 5 mM MgCl$_2$, 1 mM DTT, 5% glycerol). Reactions were allowed to incubate at room temperature for 10 minutes prior to incubation for 30 minutes with an equal volume of amylose resin (NEB) pre-equilibrated in 1× binding buffer. Protein DNA complexes were removed by low-speed centrifugation and aliquots of supernatant were removed for subsequent processing.

Reassembly and Amplification

Supernatant (50 µL) from consensus filtering experiments was desalted using Centri-Sep spin columns (Princeton Separations) and concentrated. Purified and concentrated DNA fragments were reassembled as above with aliquots removed at varying cycles. Aliquots of assembly reactions were resolved on 2% agarose gels to monitor the reassembly process. Aliquots showing predominantly reassembled full-length GFPuv were PCR amplified as above. Aliquots of supernatant from coincidence filtering experiments were diluted 10-fold and PCR amplified as above.

Cloning

PCR products were digested with Bai nHl/EcoRl (Promega) and ligated into the 2595 bp BamHl-EcoRl fragment of pGFPuv. Ligations were transformed into E. coli DH5 and fluorescent colonies were scored using a handheld 365 nm UV lamp.

We claim:

1. A method for using consensus shuffling to produce an error-reduced double stranded DNA target sequence, the method comprising the steps of:
    (a) providing at least one double stranded DNA molecule having a predefined target sequence, wherein the predefined target sequence has at least one error in said target sequence, and wherein the error comprises a sequence mismatch between the duplex strands;
    (b) digesting the double stranded DNA molecule of step (a) with at least two endonucleases into smaller overlapping duplex DNA molecules, such that at least one of the smaller overlapping duplex DNA molecules contains a sequence mismatch between its duplex strands;
    (c) exposing the digested smaller duplex DNA molecules to a DNA binding agent which binds selectively to duplex DNA molecules having a sequence mismatch between their duplex strands for the purpose of removing the smaller duplex DNA molecules having the sequence mismatch;
    (d) separating the digested and bound smaller duplex DNA molecules having a sequence mismatch away from the digested smaller duplex DNA molecules of correct sequence, wherein the remaining smaller duplex DNA molecules are enriched in the correct target sequence; and
    (e) assembling the double stranded DNA molecule having an error-reduced target sequence by hybridizing the overlapping smaller duplex DNA molecules of step (d) which are enriched for the correct target sequence to each other, and using the resulting hybridized DNA molecules as templates in PCR to amplify the enriched DNA molecules into the double stranded DNA molecule having an error-reduced target sequence.

2. A method as claimed in claim 1 wherein the separation is performed by affinity binding the DNA binding agent at a fixed location.

3. A method as claimed in claim 1 wherein the separation is performed by electrophoresis.

4. A method as claimed in claim 1 wherein the DNA binding agent is MutS.

5. A method as claimed in claim 1 wherein the steps (b) through (e) are performed repetitively until a desired level of purity of DNA molecules having the error-reduced target sequence is achieved.

6. A method as claimed in claim 1 wherein step (a) is performed by synthesizing in parallel a plurality of single stranded oligonucleotides and then permitting the single stranded oligonucleotides to hybridize to each other to make the double stranded DNA molecule.

7. A method as claimed in claim 6 wherein the step of synthesizing a plurality of single stranded oligonucleotides is performed by using a maskless array synthesizer instrument to make a DNA microarray with a plurality of single stranded oligonucleotides on a substrate and then releasing the oligonucleotides from the substrate.

8. A method for using consensus shuffling to produce a double stranded DNA molecule having an error-reduced target sequence, the method comprising the steps of:
(a) providing at least one double stranded DNA molecule having a predefined target sequence, wherein the predefined target sequence has at least one error in said target sequence, and wherein the error comprises a sequence mismatch between the duplex strands;
(b) digesting the double stranded DNA molecule of step (a) with at least two endonucleases into smaller overlapping duplex DNA molecules, such that at least one of the smaller duplex DNA molecules contains a sequence mismatch between its duplex strands;
(c) exposing the digested smaller duplex DNA molecules to a DNA binding agent which will bind selectively to smaller duplex DNA molecules having a sequence mismatch between their duplex strands for the purpose of removing the smaller duplex DNA molecule having the sequence mismatch;
(d) separating the digested and bound smaller duplex DNA molecules having a sequence mismatch away from the digested smaller duplex DNA molecules of correct sequence, wherein the remaining smaller duplex DNA molecules are enriched in the correct target sequence; and
(e) assembling the double stranded DNA molecule having an error-reduced target sequence by hybridizing the smaller duplex DNA molecules of step (d) which are enriched for the correct sequence to each other, and using the hybridized DNA molecules as templates in PCR to amplify the enriched DNA molecules into the double stranded DNA molecule having an error-reduced target sequence;
(f) repetitively performing steps (b) through (e) until a desired level of purity of the double stranded DNA molecules having an error-reduced target sequence is achieved.

9. A method as claimed in claim 8 wherein the separation is performed by affinity binding the DNA binding agent at a fixed location.

10. A method as claimed in claim 8 wherein the separation is performed by electrophoresis.

11. A method as claimed in claim 8 wherein the first and second DNA binding agents is MutS.

12. A method as claimed in claim 8 wherein step (a) is performed by synthesizing in parallel a plurality of single stranded oligonucleotides and then permitting the single stranded oligonucleotides to hybridize to each other to make the double stranded DNA molecule.

13. A method as claimed in claim 12 wherein the step of synthesizing a plurality of single stranded oligonucleotides is performed by using a maskless array synthesizer instrument to make a DNA microarray with a plurality of single stranded oligonucleotides on a substrate and then releasing the oligonucleotides from the substrate.

14. A method for assembling a DNA molecule having a predefined target sequence using the process of consensus shuffling, the method comprising:
(a) providing at least one double stranded DNA molecule having a predefined target sequence, wherein the predefined target sequence has at least one error in said target sequence, and wherein the error comprises a sequence mismatch between the duplex strands;
(b) digesting the double stranded DNA molecule of step (a) with at least two endonucleases into smaller overlapping duplex DNA molecules, such that at least one of the smaller duplex DNA molecules contains a sequence mismatch between its duplex strands;
(c) exposing the digested smaller duplex DNA molecules to a DNA binding agent which binds selectively to duplex DNA molecules having a sequence mismatch between their duplex strands for the purpose of removing the smaller duplex DNA molecules having the sequence mismatch;
(d) separating the digested and bound smaller duplex DNA molecules having a sequence mismatch away from the smaller duplex DNA molecules having the correct target sequence, wherein the remaining smaller duplex DNA molecules are enriched in the correct target sequence; and
(e) assembling a double stranded DNA molecule having an error-reduced predefined target sequence by hybridizing the smaller duplex DNA molecules of step (d) which are enriched for the correct target sequence to each other, and using the hybridized DNA molecules as templates in PCR to amplify the enriched DNA molecules into the double stranded DNA molecule having the error-reduced predefined target sequence.

15. A method for assembling a DNA molecule having a predefined target DNA sequence using the process of consensus shuffling, the method comprising:
(a) providing at least one double stranded DNA molecule having a predefined target sequence, wherein the predefined target sequence has at least one error in said target sequence, and wherein the error comprises at least one sequence mismatch between the duplex strands;
(b) digesting the double stranded DNA molecule with at least two endonucleases into smaller overlapping duplex DNA molecules, such that at least one of the duplex DNA molecules contains a sequence mismatch between its duplex strands;
(c) exposing the digested DNA molecules to a DNA binding agent which binds selectively to duplex DNA molecules having a sequence mismatch between their duplex strands for the purpose of removing the smaller duplex DNA molecules containing the mismatches;
(d) separating the digested and bound smaller duplex DNA molecules having a sequence mismatch away from the digested smaller duplex DNA molecules having the correct target sequence, wherein the remaining smaller duplex DNA molecules are enriched in the correct target sequence;
(e) assembling a double stranded DNA molecule having an error-reduced predefined target sequence by hybridizing the overlapping smaller duplex DNA molecules of step (d) which are enriched for the correct target sequence to each other, and using the hybridized DNA molecules as templates in PCR to amplify the enriched DNA molecules into the double stranded DNA molecule having the error-reduced predefined target sequence;

(f) repetitively performing steps (b) through (e) until a desired level of purity of the a consensus sequence is achieved.

* * * * *